(12) United States Patent
Bock et al.

(10) Patent No.: US 7,648,476 B2
(45) Date of Patent: Jan. 19, 2010

(54) BLOOD TREATMENT APPARATUS WITH ALARM DEVICE

(75) Inventors: Gerhard Bock, Friedwald (DE); Günter Niemetz, Melsungen (DE); Sándor Dolgos, Szentendre (HU); Róbert Schin, Budapest (HU)

(73) Assignee: B. Braun Medizintechnologie GmbH, Melsungen (DE)

( * ) Notice: Subject to any disclaimer, the term of this patent is extended or adjusted under 35 U.S.C. 154(b) by 67 days.

(21) Appl. No.: 11/386,614

(22) Filed: Mar. 22, 2006

(65) Prior Publication Data

US 2007/0000824 A1    Jan. 4, 2007

(30) Foreign Application Priority Data

Mar. 23, 2005   (DE) ...................... 10 2005 013 418

(51) Int. Cl.
*A61M 37/00* (2006.01)
*A61M 1/00* (2006.01)

(52) U.S. Cl. .................... 604/4.01; 604/6.01; 604/6.09; 604/6.1; 604/6.11; 604/6.14; 422/44

(58) Field of Classification Search .............. 604/6.06, 604/6.11, 6.16, 4.01, 5.01, 5.04, 6.09, 6.1; 422/48
See application file for complete search history.

(56) References Cited

U.S. PATENT DOCUMENTS

| | | | |
|---|---|---|---|
| 3,641,570 A * | 2/1972 | Thompson | 340/508 |
| 4,221,543 A * | 9/1980 | Cosentino et al. | 417/22 |
| 4,231,366 A * | 11/1980 | Schael | 604/6.05 |
| 4,324,663 A * | 4/1982 | Hirel et al. | 210/646 |
| 4,401,971 A * | 8/1983 | Saito et al. | 340/460 |
| 4,582,598 A * | 4/1986 | Bilstad et al. | 210/101 |
| 4,653,003 A * | 3/1987 | Kirstein | 701/29 |
| 4,812,819 A * | 3/1989 | Corsberg | 340/517 |
| 5,103,214 A * | 4/1992 | Curran et al. | 340/691.1 |
| 5,368,555 A * | 11/1994 | Sussman et al. | 604/6.05 |
| 5,487,827 A * | 1/1996 | Peterson et al. | 210/87 |
| 5,618,441 A * | 4/1997 | Rosa et al. | 210/739 |
| 5,629,871 A * | 5/1997 | Love et al. | 702/34 |
| 5,679,245 A * | 10/1997 | Manica | 210/134 |
| 5,762,805 A * | 6/1998 | Truitt et al. | 210/645 |
| 5,788,851 A * | 8/1998 | Kenley et al. | 210/739 |
| 6,146,523 A * | 11/2000 | Kenley et al. | 210/143 |
| 6,780,322 B1 * | 8/2004 | Bissler et al. | 210/637 |
| 6,923,782 B2 * | 8/2005 | O'Mahony et al. | 604/4.01 |
| 2003/0128125 A1 * | 7/2003 | Burbank et al. | 340/605 |
| 2003/0217972 A1 * | 11/2003 | Connell et al. | 210/646 |
| 2003/0220598 A1 * | 11/2003 | Busby et al. | 604/5.01 |
| 2004/0167465 A1 * | 8/2004 | Mihai et al. | 604/67 |
| 2004/0254514 A1 * | 12/2004 | Gura | 604/5.01 |
| 2005/0085760 A1 * | 4/2005 | Ware et al. | 604/4.01 |

FOREIGN PATENT DOCUMENTS

DE    19901288    7/2000

* cited by examiner

*Primary Examiner*—Leslie R Deak
*Assistant Examiner*—Adam Marcetich
(74) *Attorney, Agent, or Firm*—RatnerPrestia

(57) ABSTRACT

A blood treatment apparatus includes a controller and a supervisor, which together monitor various sensors. The controller is equipped with a first alarm system and the supervisor is equipped with a second alarm system. To avoid competition between both alarm systems, the alarm system of the supervisor normally remains mute. A function monitoring device monitors the function of the first alarm system and signals a missing alarm to the supervisor. Only in this case will the second alarm system of the supervisor be activated.

8 Claims, 6 Drawing Sheets

BLOOD TREATMENT APPARATUS WITH ALARM DEVICE

CROSS-REFERENCE TO RELATED APPLICATION

This application is a direct National Stage filing of German Patent Application No. 10 2005 013 418.1, filed on Mar. 23, 2005.

FIELD OF THE INVENTION

The invention refers to a blood treatment apparatus with a blood circuit and a dialysate circuit, sensors for monitoring parameters of the blood treatment apparatus and/or the patient, and actors for effecting changes in the circuits, a controller for monitoring the signals supplied by the sensors and for controlling the actors, a first alarm system controlled by the controller, a supervisor controlling the controller, and a second alarm system controlled by the supervisor, the controller and the supervisor being able to detect alarm conditions.

BACKGROUND OF THE INVENTION

In a blood treatment apparatus with an extracorporeal blood circuit, such as a dialysis apparatus, numerous monitoring operations have to be performed to protect the patient or the operator from possible hazards. To this end, the blood treatment apparatus is equipped with a plurality of sensors that monitor various parameters such as pressures, temperatures, conductivity or flow and perform a control or a switching operation in dependence on the result. It is common that certain single parameters or limit values are entered into the apparatus by the operating personnel and that the apparatus monitors the adherence to the parameters and limit values during operation. Upon occurrence of an unacceptable deviation, the apparatus is transferred into a safety state and an issuing of an alarm calls the personnel to the apparatus to take the necessary measures for the treatment to be continued. Usually, a nurse takes care of a number of patients so that he or she cannot immediately give his or her attention to the patient or the apparatus every time an alarm occurs. It is common to differentiate the sounds of acoustic alarms so that in the event of a plurality of simultaneous alarms from different apparatus, a nurse can immediately determine which alarm or which apparatus has the higher priority.

In a blood treatment apparatus it is known to provide a controller for controlling and monitoring which receives and processes the signals from the sensors and is connected with a first alarm system. The high safety requirements for such an apparatus make it imperative to monitor the controller for the fulfillment of its function. This is effected by a supervisor, which also receives sensor signals and, using function redundancy, checks whether the controller responds appropriately in each individual case. The controller and the supervisor are processors that function independent from each other and mutually control each other. The supervisor is also equipped with an alarm system.

Generally, dialysis treatments are performed in dialysis centers. Typically, they have 20 to 50 treatment places distributed over a plurality of rooms. The attendant personnel performs the treatment according to a doctor's treatment schedule or on direct instructions. The part of the treatment schedule that is related to the apparatus is entered into the apparatus as setting parameters. The inputted parameters are monitored by the apparatus during the treatment. Upon an unacceptable deviation, a safe mode for the patient is assumed and the attendant personnel is called to the apparatus to take measures that allow the treatment to be continued. Usually, one nurse attends to several patients and cannot immediately give her or his attention to the patient or the apparatus on every alarm. To prevent this from resulting in hazards to the patient, the sound or the optical appearance of the alarm signals are varied according to the urgency of the treatment abnormality.

In a dialysis apparatus, concentrates and water are mixed to supply the dialyser with hemodialysis solution. Separated by a membrane, the blood flows in the dialyser in a direction opposite to the hemodialysis solution. In the process, contaminants are removed from the blood through the hemodialysis solution. Usually, one dialysis treatment session takes four to six hours. During this period of time, conditions may arise that cannot be controlled by the dialysis apparatus. Such conditions include, for example:

arterial pressure is too negative due to an obstruction in the arterial line of the extracorporeal circuit upstream of the blood pump;

venous pressure is too low due to a venous needle having slipped out of the patient access;

no water in the supply line;

concentrate container is empty; and no voltage supply.

To detect such conditions that are hazardous to patients, dialysis apparatuses are equipped with two independent alarm systems so that they can still operate safely should one component be defective. The following functions are given in each alarm system:

storing the limit values for the parameters to be controlled;

transducers for the parameters to be monitored;

processing of measured values for the parameters to be monitored;

comparison of the measured values to the associated limit values;

control of the actors to assume a safe treatment mode (blood pump stop;

bypass of the hemodialysis solution at the dialyser);

optical indication of the alarm condition; and acoustic indication of the alarm condition.

Usually, the acoustic alarm alerts the attendant personnel to the irregular state of the apparatus. It is irritating when an alarm condition has already been signaled by the first alarm system and the second alarm system also signals the same condition, since this suggests greater urgency to the attendant personnel although this is not necessary.

DE 199 01 288 A1 describes a device for monitoring loudspeakers with which the functionality of individual loudspeakers can be monitored by recording an acoustic signal emitted by the loudspeaker. Thus, the failure of a loudspeaker can be detected.

BRIEF SUMMARY OF THE INVENTION

The present invention provides a blood treatment apparatus comprising a blood circulator, a dialysate circulator, sensors for monitoring parameters, and actors for effecting changes in the circulators. The apparatus also includes a controller for monitoring signals supplied from the sensors and for controlling the actors, a first alarm system controlled by the controller, a supervisor monitoring the controller, a second alarm system controlled by the supervisor, the controller and the supervisor being configured to detect alarm conditions, and a function monitoring device. Upon detection of an alarm condition by at least one of the controller and the supervisor, the first alarm system is activated, and wherein, in case of a failure of the first alarm system, the function monitoring device activates the second alarm system through the supervisor.

The invention provides that the acoustic signaling is performed through the first alarm system and that the supervisor monitors the correct functioning of this alarm system. Thus, it is guaranteed that only one of the alarm systems is activated and that no competition between both alarm systems occurs. This avoids confusion of the attendant personnel. The attendant personnel is assisted in removing alarm conditions in a stress-free manner. Unnecessary manipulations are avoided. The invention is particularly suitable for such blood treatment apparatus that are set up in a dialysis center, but it also applicable to an individual apparatus.

It is possible that several alarm conditions are signaled at the same time at the same blood treatment apparatus. In such an event, it is important to signal and remove the more dangerous alarm condition first. In an advantageous embodiment of the invention it is provided that the alarm conditions are divided in different alarm stages depending on the signals from the sensors, wherein the alarm condition with the highest alarm stage is activated should several alarm conditions be present at the same time. This means that the alarm with the highest alarm stage activates the alarm system of the controller and that the alarm is simultaneously indicated at an operator device forming the operator interface, possibly together with counter measures that must be taken by the attendant personnel. As soon as the alarm condition with the highest alarm stage has been removed, the alarm condition with the next highest priority is indicated. This allows for an orderly working off of the individual alarm conditions.

According to an exemplary embodiment of the invention, an alarm table is formed in the controller and in the supervisor, respectively, which includes those alarm conditions that are detected by the sensors of the controller or the supervisor. In addition, both alarm tables may be synchronized. Synchronizing means that an alarm table that does not include an alarm condition is completed, wherein this alarm condition is added to the alarm table. In any case it is made sure that both alarm tables are identical so that the supervisor can also monitor the correct issuing of an alarm by the controller.

The alarm stages may have different sound patterns as to their frequencies and/or tonal rhythms or sound characteristics.

Suitably, an alarm acknowledgement key is provided, the actuation of which halts the issuing of an alarm for a predetermined time. This guarantees that the operator can first deactivate the issuing of the alarm, before removing the trouble or taking the necessary measures at the patient. Thus, the necessary quiet is established. Upon the lapse of the predetermined period, however, the alarm will be issued again should it not have been removed before then.

BRIEF DESCRIPTION OF THE FIGURES

The following is a detailed explanation of an embodiment of the present invention with reference to the drawings. In the Figures.

DETAILED DESCRIPTION OF THE INVENTION

Figure 1:
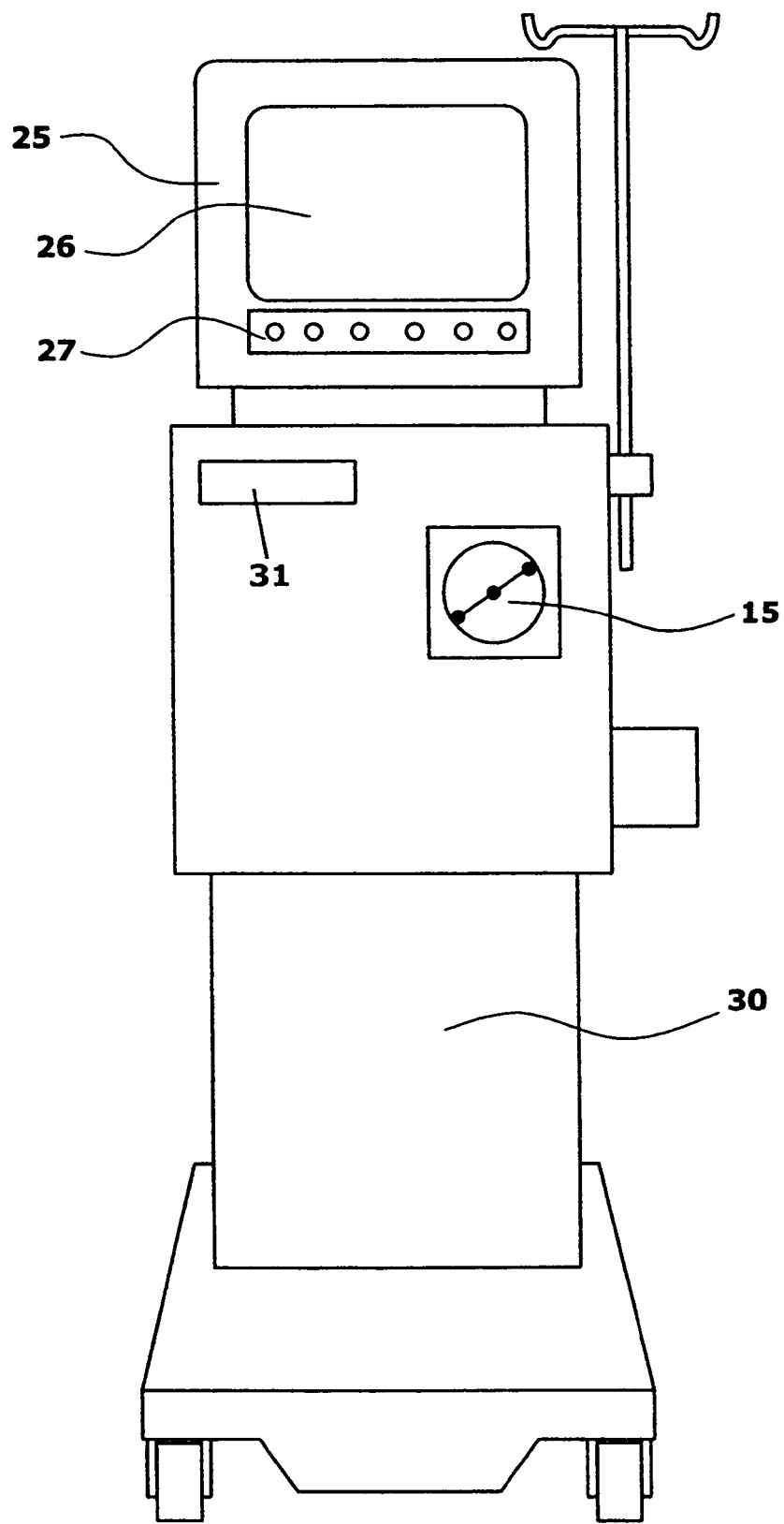
FIG. 1 is an overall view of the blood treatment apparatus.

A blood treatment apparatus illustrated in FIG. 1 is displaceable on rollers. The apparatus comprises a base 30. A blood pump 15, which is a hose pump, is arrange at the front side of a housing. At the top end of the housing, a syringe pump 31 is situated. Mounted on the housing is the operator device 25 having a monitor 26 and an operating part 27 having a plurality of keys. The dialysate is prepared within the housing. The apparatus is connected to the blood circulator of a patient through hoses.

Figure 2:
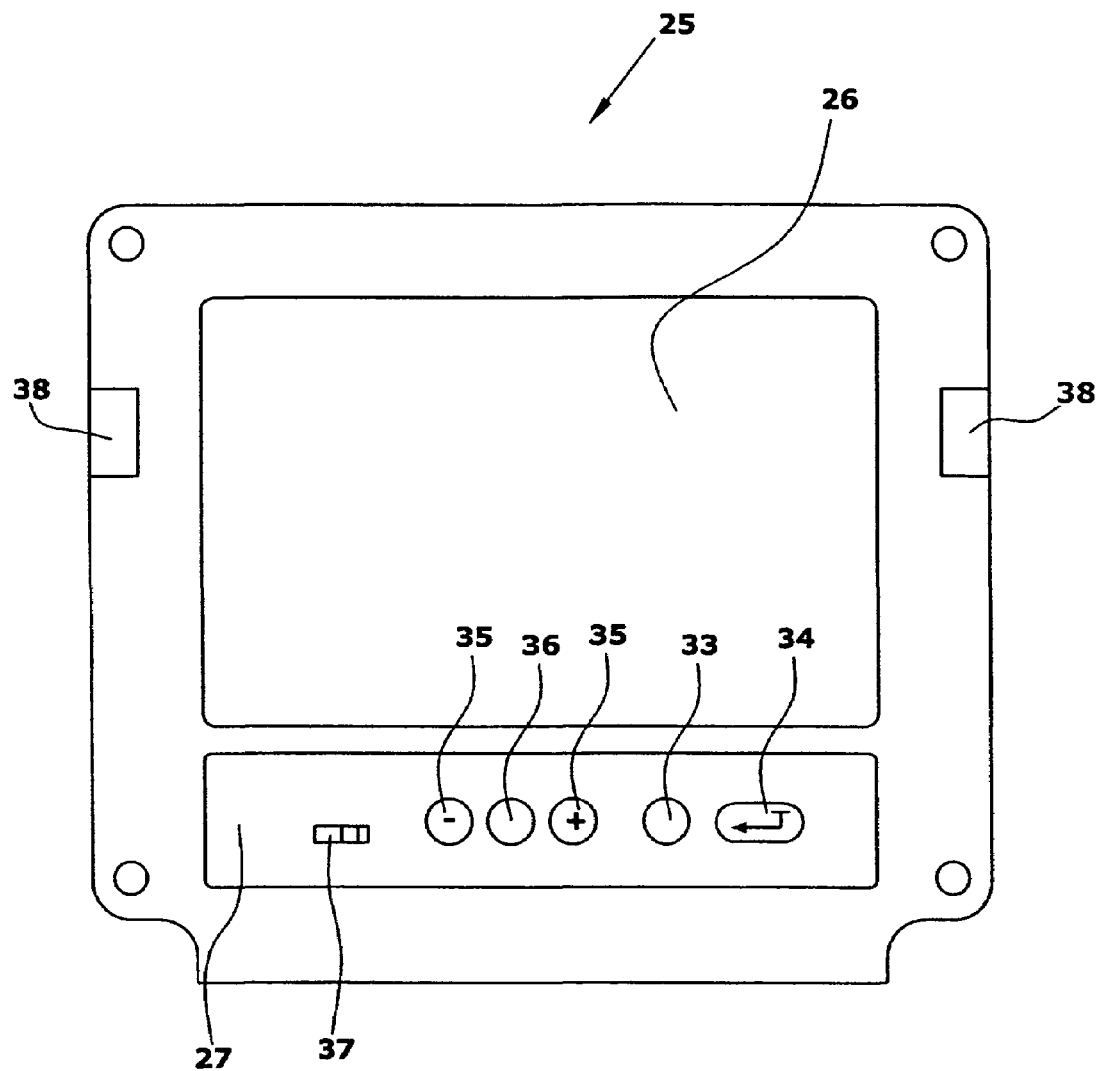
FIG. 2 is an illustration of the operator device.

FIG. 2 illustrates the operator device 25 with the monitor 26, which is configured as a touch-screen, and the operating part 27 situated below the same. The operating part 27 includes an alarm acknowledgement key 33, an enter key 34 as well as input keys 35 for increasing or decreasing input values for the blood pump, a start/stop key 36 for the blood pump, and a battery condition light 37. Signal lights 38 are mounted at the sides of the operator device 25. The signal lights 38 are green when they indicate a no-alarm condition. The signal lights 38 shine red to indicate an alarm condition.

Figure 3:
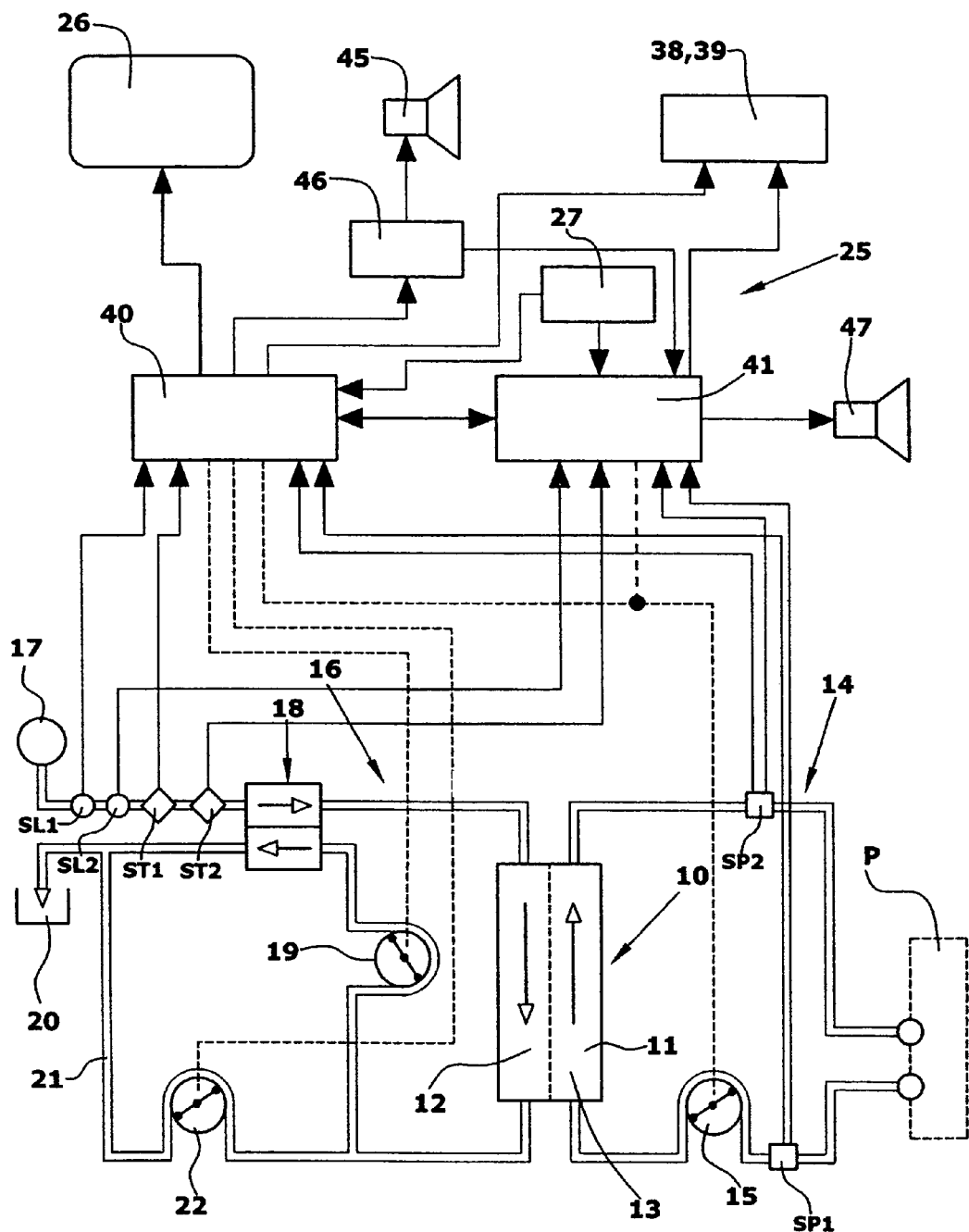
FIG. 3 is a schematic illustration of the control and monitoring system.

FIG. 3 is a schematic illustration of the circulation system of the dialysis machine. The dialysis machine comprises a dialyser 10 having a first chamber 11 and a second chamber 12 separated from each other by a dialysis membrane 13. The first chamber 11 is a blood chamber which is part of a blood circulator 14. The blood circulator 14 leads from the body of a patient P via a blood pump 15 through the chamber 11 back to the patient. The second chamber 12 is part of a dialysate circulator 16 leading through the second chamber 12. The dialysate circulator 16 leads from a dialysate source 17, supplying hemodialysis solution, through a balancing means 18 to the second chamber 12 and from there to the balancing means 18 via a dialysate pump 19 and finally into a drain 20. The balancing means 18 has the effect that the amount of liquid discharged is the same as the amount of liquid supplied. Downstream of the dialyser 10 a bypass line 21 is branched off which includes another pump 22 and leads directly into the drain 20. The bypass line 21 is an ultrafiltration line. By adjusting the output volume of the pump 22, the ultrafiltration volume can be determined, i.e. the volume that is additionally transferred into the dialysate circulator through the membrane 13 of the dialyser.

All pumps 15, 19 and 22 are volumetric pumps or displacement pumps wherein the output volume is proportional to the pump speed. The pump speeds are controlled by the control part of the operator device 25 having a display device in the form of monitor 26 and by the operating part 27 having a plurality of keys. The monitor 26 forms the operator interface for setting and adjusting machine parameters and for informing the operator about the functioning of the dialysis machine.

The operator device 25 includes a first processor which is referred to as a controller 40 and a second processor which is referred to as a supervisor 41. The controller 40 is connected to the monitor 26. It serves the internal control of the blood treatment apparatus and the various components included therein. A plurality of sensors are accommodated in the blood treatment apparatus, of which only a few are represented in the drawing. Among these are conductivity sensors SL1 and SL2 and temperature sensors ST1, ST2 in the line between the dialysate source 17 and the balancing means 18, as well as a pressure sensor SP1 in the arterial blood line and a pressure sensor SP2 in the venous blood line of the blood circulator 14. The total number of sensors present, which monitor different functions and parameters, including the preparation of the dialysate in the dialysate source 17, generally is 30-40. The signals from the sensors are supplied to the controller 40. Some of these signals are also supplied to the supervisor 41. Of the two conductivity sensors SL1 and SL2 and the two temperature sensors ST1, ST2, a respective one (SL1, ST1) is connected to the controller 40 and the other one (SL2, ST2) is connected to the supervisor 41. These sensors are provided twice so that the failure of one of these sensors is detected. Other sensors provide their output signals both to the controller 40 and to the supervisor 41.

The controller 40 is an independently functional control unit for controlling all functions of the apparatus. It controls the pumps 15, 19 and 22 and controls all processes in the apparatus according to the parameters set by the operator and to the respective mode set.

The controller 40 is provided with an alarm system 45 of its own which is equipped with a function monitoring device 46. The output signal from the function monitoring device 46 is supplied to the supervisor 41. The latter is equipped with an alarm system 47 of its own. The alarm systems 45 and 47 each have an acoustic alarm device that can produce alarms of different alarm stages. The alarm stages differ in the frequency or tone or the tonal rhythm of the sound signals.

The treatment parameters entered by the operator, e.g. target values or limit values, are stored both in the controller and in the supervisor. During the treatment of the patient, a two-channel monitoring is performed, specifically by the controller and the supervisor. In the controller 40 and the supervisor 41, the values supplied by the individual sensors are compared to the associated limit values. When a sensor value is outside the predetermined limits, a mode that is safe for the patient is set. This is effected according to the position of the sensor. If, for example, a limit value is exceeded in preparing the hemodialysis solution, the hemodialysis solution is routed past the dialyser through a bypass (not illustrated). This is effected by switching corresponding valves. In the blood circulator, the blood pump 15 and a syringe pump 31 are stopped and corresponding hose clamps (not illustrated) are closed. Simultaneously, the signal lights 38, 39 are switched to red.

Thereafter, the controller 40 and the supervisor 41 perform an update of the alarm table, noting and storing the respective condition. The alarm stage of the respective alarm is also noted in the alarm table. The alarm stages are divided into: high, medium and low priority.

Table 1 below lists the possible consequences that may occur if no response is made to an alarm. The different priorities or alarm stages result therefrom.

TABLE 1

| Possible consequence of not responding to an Alarm | Beginning of possible damage | | |
|---|---|---|---|
| | immediate | prompt | delayed |
| Death or irreversible injury | High priority | High priority | Medium priority |
| Reversible injury | High priority | Medium priority | Low priority |
| Minor injury | Medium priority | Medium priority | Low priority |

The acoustic alerting is first performed according to the highest alarm stage entered in the alarm table. The signaling through loudspeakers is performed in pulsed operation, individual tones being separated by pauses. Different signal patterns may be produced corresponding to the respective alarm stage.

When the controller 40 has detected an alarm situation, the same is communicated to the supervisor. The supervisor checks the issuing of the alarm by means of a current measurement.

Figure 4:
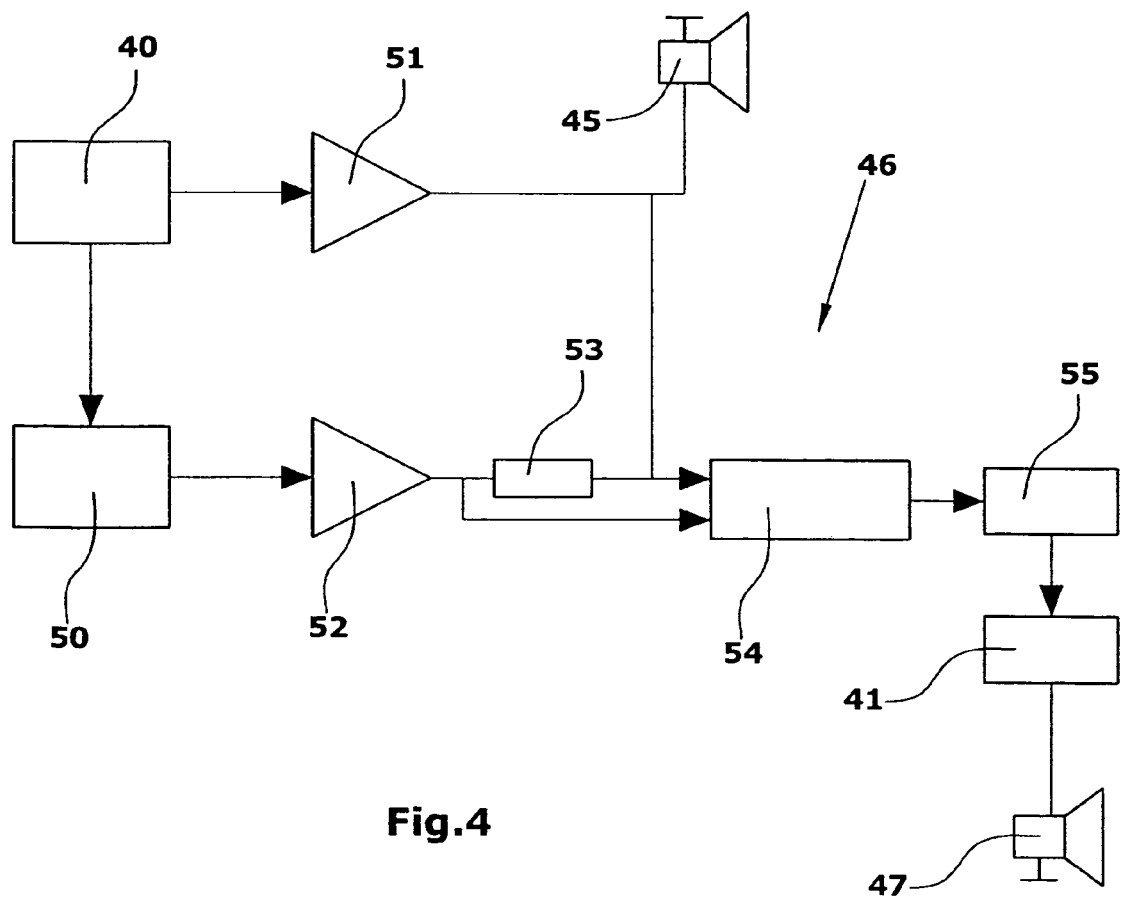
FIG. 4 is a schematic illustration of the function monitoring device for the first alarm system.

FIG. 4 illustrates the function monitoring device 46 of the alarm system 45. The alarm signals produced by the controller 40 are supplied to a frequency generator 50 and, further, to an amplifier 51 to control the alarm system 45. The loudspeaker electric current of the alarm system 45 is measured as the voltage drop across the resistor 53 whereby the voltage inputted into the resistor 53 from the amplifier 52 is dependent upon the frequency from the frequency generator 50. The measuring circuit 54 measures the loudspeaker current and the frequency of the loudspeaker signals. Both are converted into digital signals by an A/D converter 55 and are supplied to the supervisor 41. The latter thus monitors the signal generation and also the correctness of the respective alarm signal. If the alarm signal is correct, the second alarm system 47 is not actuated by the supervisor 41. The supervisor 41 actuates the alarm system 47 only when the first alarm system 45 was not activated in spite of the presence of an alarm condition. Thus, among others, the supervisor also monitors the functioning of the loudspeaker in the alarm system 45. Should the loudspeaker be defective, this is detected by the loudspeaker current being missing.

If a nurse is present at the blood treatment apparatus to remove the cause of the alarm, the nurse can press the alarm acknowledgement key 33 (FIG. 2) to disable the alarm system for a predetermined period of time. The cause for the alarm being removed, the nurse again presses the alarm acknowledgement key. Thereupon, the controller 40 or the supervisor 41 switches off the red signal light and the actors for the instructions from the controller are enabled again so that the treatment is continued.

Figure 5A:
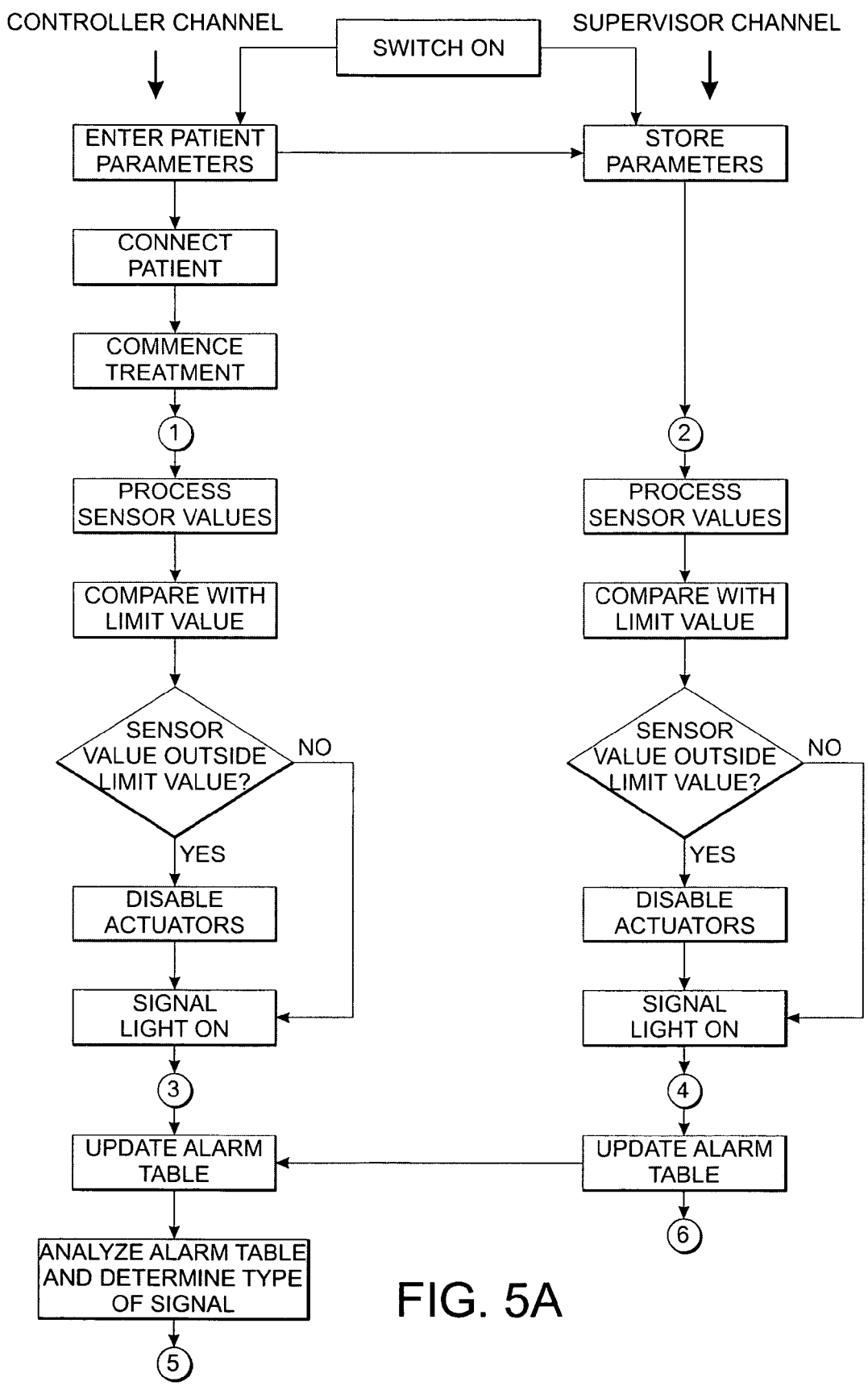
FIGS. 5a and 5b illustrate a flow diagram of the function of the controller and the supervisor.
Figure 5B:
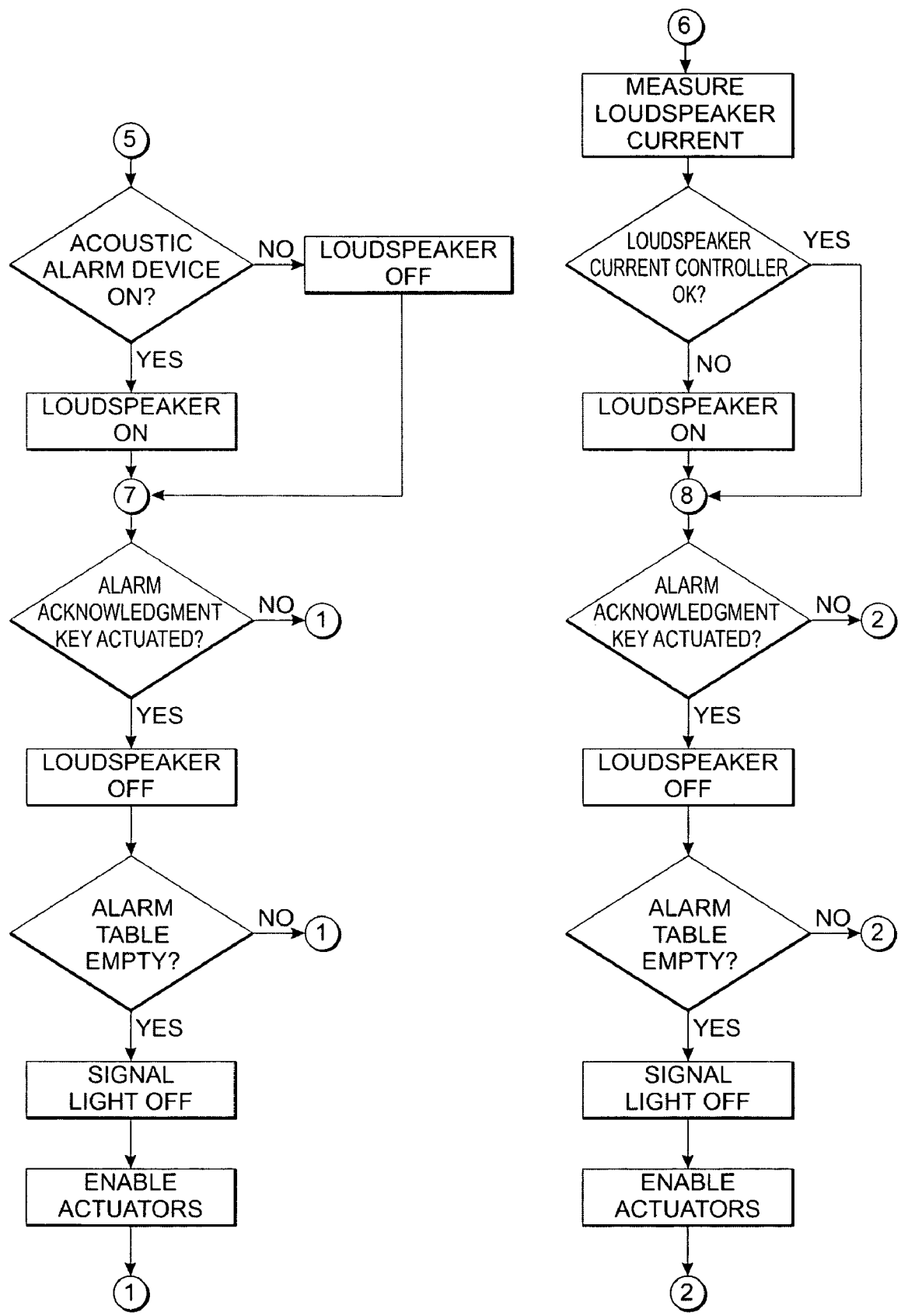

FIGS. 5a and 5b show a flow diagram of the processes in the controller channel of the controller 40 and in the supervisor channel of the supervisor 41.

The step "process sensor values" includes the sampling of all sensors. The sampling is done cyclically every 200 ms. As is obvious from FIG. 5a, the functions are generally performed in parallel in both channels. An alarm table of the alarm conditions detected is kept in both channels. Both alarm tables are compared to each other. The supervisor transmits its alarm table to the controller which enters these alarm conditions into its alarm table. It is also possible to have the alarm table of the controller transmitted to the supervisor.

As results from FIG. 5b, in a normal alarm event, only the loudspeaker of the alarm system 45 controlled by the controller is actuated, whereas the second alarm system 47 remains inactive. The second alarm system 47 of the supervisor is activated only if the loudspeaker current of the alarm system of the controller is missing or incorrect. After actuation of the alarm acknowledgement key 33, the alarm is suspended, i.e. the loudspeaker is turned off. Then, it is checked whether the alarm table is empty. If no other alarm is pending, the red signal light is deactivated and the green signal light is turned on and the apparatus returns to the states 1 and 2 in FIG. 5a.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A blood treatment apparatus comprising:
a blood circulator;
a dialysate circulator;
sensors for monitoring parameters;
actors programmed to effect changes in the circulators;
a controller programmed to detect alarm conditions for monitoring signals supplied from the sensors and for controlling the actors, each of the alarm conditions associated with a respective one of two or more different alarm stages;
a first alarm system controlled by the controller;
a supervisor programmed to detect alarm conditions for monitoring the controller;
a second alarm system controlled by the supervisor; and
a function monitoring device coupled to the controller and to the supervisor,
wherein, upon detection of an alarm condition by the supervisor, the supervisor is programmed to activate the first alarm system if the controller does not detect the alarm condition, is programmed to activate the second alarm system if the first alarm system fails to operate, is programmed to activate the second alarm system if the first alarm system actively presents an incorrect alarm stage not associated with the alarm condition, and is programmed to not activate the second alarm system if the first alarm system operates correctly based at least in part on an input from the function monitoring device.

2. The blood treatment apparatus of claim 1, wherein the alarm condition of the alarm stage having a highest priority is activated if several alarm conditions should be present at the same time.

3. The blood treatment apparatus of claim 1, further comprising an alarm table in each of the controller and the supervisor, respectively, wherein each alarm table includes the alarm conditions detected by the sensors of the controller or the supervisor, respectively.

4. The blood treatment apparatus of claim 1, wherein the alarm stages have sounds differing in frequency and/or tonal rhythm.

5. The blood treatment apparatus of claim 1, further comprising an alarm acknowledgement key, wherein operation of the alarm acknowledgement key halts the alarm for predetermined period of time.

6. The blood treatment apparatus of claim 3, wherein the alarm is issued depending on the alarm conditions contained in the alarm table.

7. The blood treatment apparatus of claim 1, wherein the sensors are sampled in fixed time intervals.

8. The blood treatment apparatus of claim 1, wherein the supervisor is programmed to activate the second alarm system if the first alarm system actively presents the incorrect alarm stage such that the second alarm system actively presents a correct alarm stage.

* * * * *